(12) United States Patent
Bennett

(10) Patent No.: US 9,024,741 B2
(45) Date of Patent: May 5, 2015

(54) STEERING WHEEL COVER DRIVER SAFETY SYSTEM

(71) Applicant: William Bennett, East Sandwich, MA (US)

(72) Inventor: William Bennett, East Sandwich, MA (US)

(*) Notice: Subject to any disclaimer, the term of this patent is extended or adjusted under 35 U.S.C. 154(b) by 0 days.

(21) Appl. No.: 13/779,710

(22) Filed: Feb. 27, 2013

(65) Prior Publication Data

US 2014/0300458 A1      Oct. 9, 2014

(51) Int. Cl.
| | | |
|---|---|---|
| *B60Q 1/00* | (2006.01) |
| *B60Q 5/00* | (2006.01) |
| *B62D 1/06* | (2006.01) |
| *B62D 15/02* | (2006.01) |
| *A61B 5/18* | (2006.01) |
| *A61B 5/11* | (2006.01) |
| *G08B 21/06* | (2006.01) |

(52) U.S. Cl.
CPC ......... *B60Q 5/005* (2013.01); *B62D 1/06* (2013.01); *B62D 15/029* (2013.01); *A61B 5/18* (2013.01); *G08B 21/06* (2013.01); *A61B 5/1125* (2013.01)

(58) Field of Classification Search
None
See application file for complete search history.

(56) References Cited

U.S. PATENT DOCUMENTS

| | | | | |
|---|---|---|---|---|
| 4,581,954 | A * | 4/1986 | Uchida | 74/552 |
| 5,042,318 | A * | 8/1991 | Franz | 74/558 |
| 6,748,822 | B2 * | 6/2004 | Hussy | 74/558 |
| 8,405,496 | B2 * | 3/2013 | Bennett | 340/439 |
| 8,564,424 | B2 * | 10/2013 | Evarts et al. | 340/439 |
| 2003/0121360 | A1 * | 7/2003 | Hussy | 74/558 |
| 2011/0115617 | A1 * | 5/2011 | Bennett | 340/439 |
| 2011/0121961 | A1 * | 5/2011 | Bennett | 340/439 |
| 2011/0133919 | A1 * | 6/2011 | Evarts et al. | 340/439 |
| 2011/0257846 | A1 * | 10/2011 | Bennett | 701/45 |

* cited by examiner

*Primary Examiner* — Travis Hunnings
(74) *Attorney, Agent, or Firm* — Kenneth Bower; Lyman H. Smith

(57) ABSTRACT

A steering wheel cover that houses the sensor, indicator, power and communication elements of a driver safety system is disclosed. The objective is to discourage texting, eating, primping one's self and cell phone use that distract drivers and causes accidents. The steering wheel cover is light, easy to install and lock in place but strong and difficult to forcibly remove. The driver safety system senses the positions of the driver's hands on the wheel rewarding safe habits. When the system senses bad habits the driver is warned, incidence is recorded for third party information in addition to alerting and annoying dis-rewards are given.

13 Claims, 2 Drawing Sheets

STEERING WHEEL COVER DRIVER SAFETY SYSTEM

CROSS-REFERENCE TO RELATED APPLICATIONS

Figure 1A:
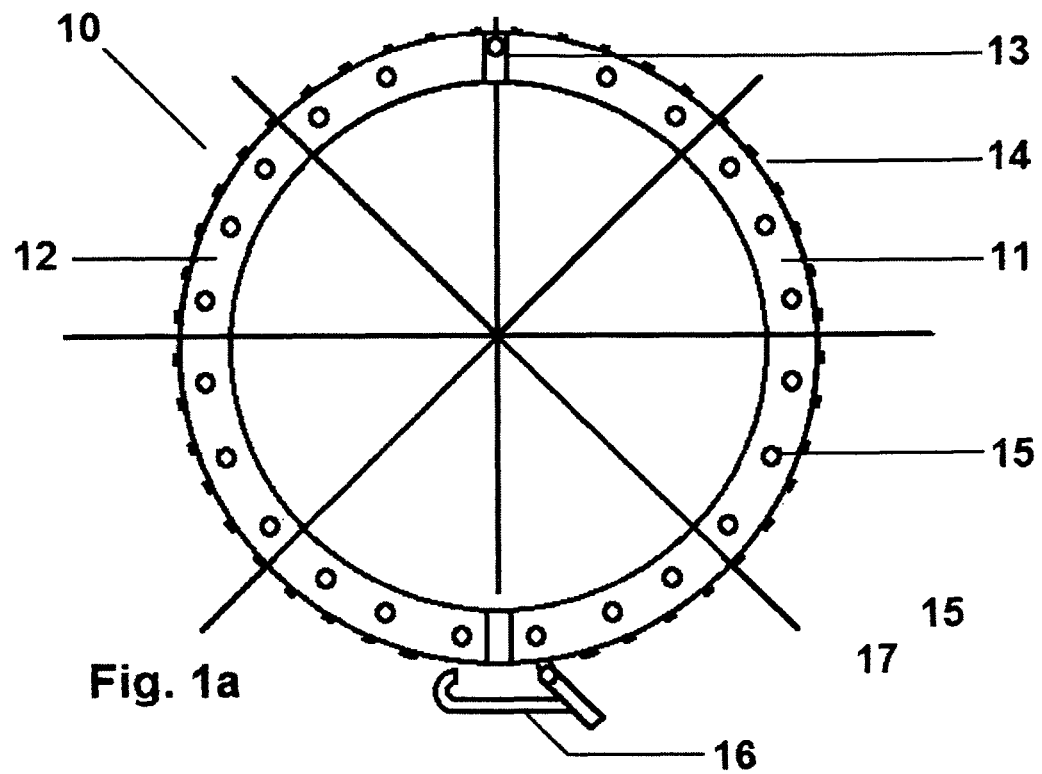

This application claims U.S. Provisional Application No. 61/603,399 filed on Feb. 27, 2012 and U.S. Non-Provisional application Ser. No. 12/618,495 filed Nov. 13, 2009.

BACKGROUND

Driver safety devices that sense bad driving habits and encourage good driving habits are under development. A major insurance company currently supplies a feedback device for monitoring the results of how the vehicle is being driven. The insurance company rewards drivers for good feed back from the device. Patent application U.S. Non-Provisional application Ser. No. 12/618,495 filed Nov. 13, 2009 is included by reference in its entirety and describes an innovative system for monitoring and recording driver habits as well as teaching and rewarding good driving habits. Devices of this type are predicted to be very unpopular with the drivers being monitored and would be removed by the driver if easy removal was possible.

Steering wheel covers of the designs that can be purchased today are very difficult to install and easy to remove. Disclosed is a steering wheel cover that is easy to install, is locked with a lock and key to the steering wheel when installation is complete and provides an ideal platform for driver safety devices that monitors driving habits.

BRIEF SUMMARY OF THE INVENTION

The present invention hosts driver safety devices in an aftermarket steering wheel cover.

The primary goal of the present invention is to attach a driver safety device to the steering wheel of an existing vehicle.

Another important goal is that the wheel cover attaches driver safety devices to a steering wheel securely, requiring a key for removal.

Another goal is to provide sensors on the steering wheel cover to monitor driver habits including distractions from eating, texting, applying make up or holding a cell phone.

Still another goal is to provide indicators that teach and encourage driving habit Safety.

Another goal is to make it difficult to circumvent the driver monitoring process and to communicate tampering to an external device.

Another goal is to have the external device to provide the only control of the turning on and off of the driver safety device as a function of the driving environment and speed of the vehicle.

Another goal is to provide a wireless transmitter and receiver for communicating data to an external device and receive operating instructions from the external device.

Still another goal is to consume miniscule power to achieve the above goals and to store, generate and otherwise provide the required power.

Another goal is to provide driving comfort to the user.

Lastly the goal is to warn that the device has been damaged, removed or disabled.

BRIEF DESCRIPTION OF THE SEVERAL VIEWS OF THE DRAWING(S)

Figure 1B:
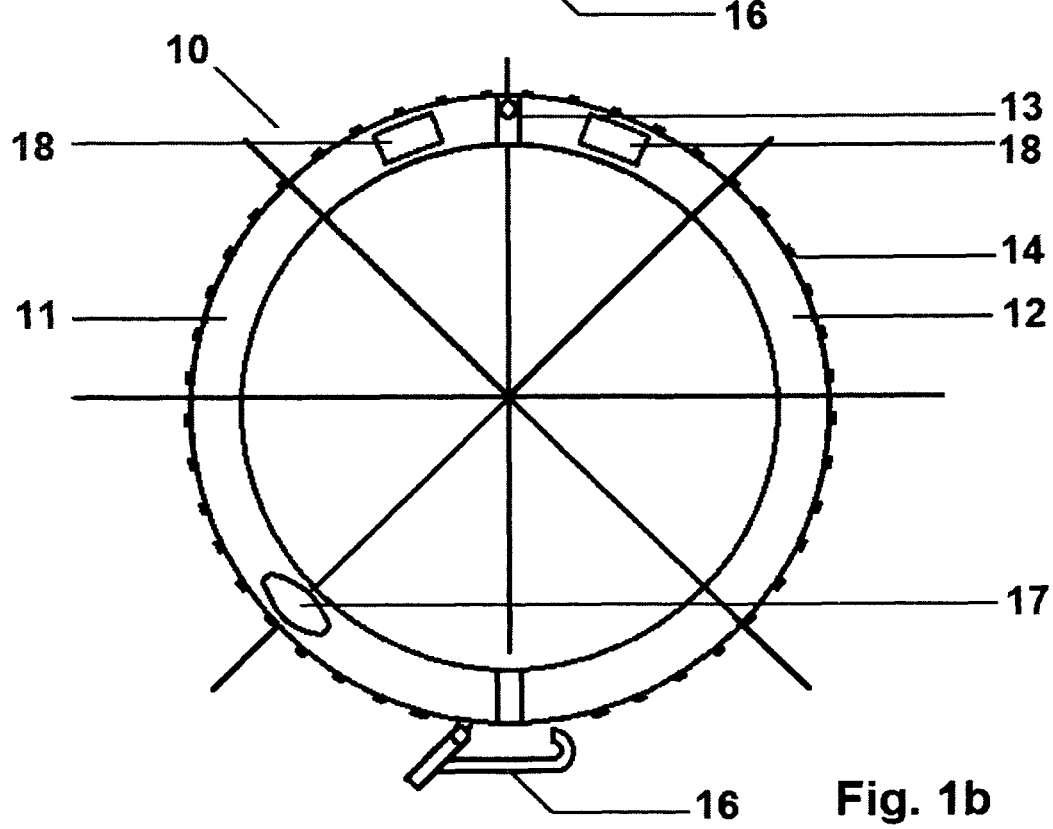
Figure 2:
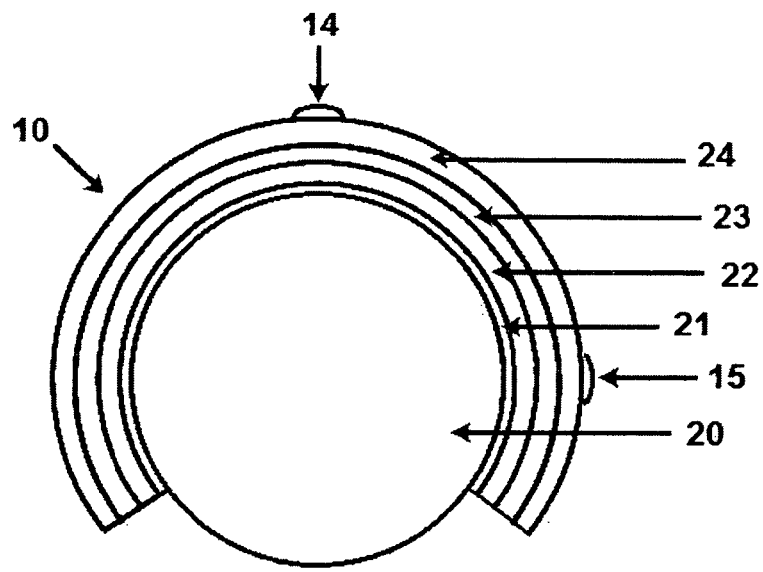
Figure 3A:
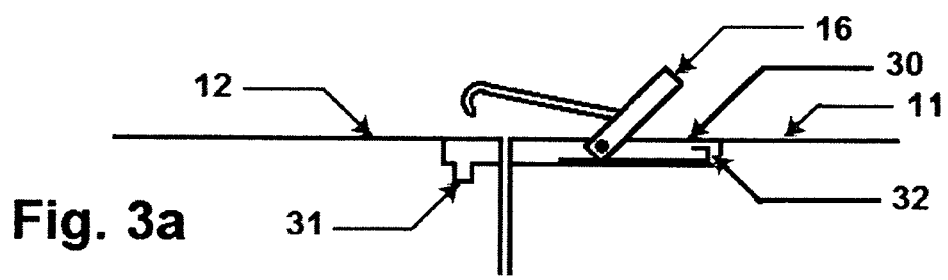
Figure 3B:
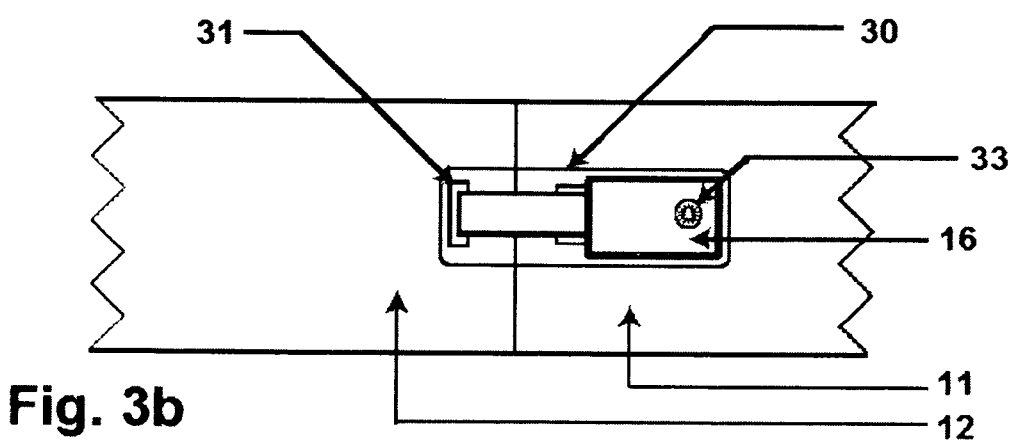

FIG. 1a: Is a front view of the present invention.
FIG. 1b: Is a rear view of the present invention.
FIG. 2: Is a sectional view of the present invention.
FIG. 3a: Is a cut away detail view of the draw latch mechanism.
FIG. 3b: Is a top detail view of the draw latch mechanism.

DETAILED DESCRIPTION OF THE INVENTION

FIG. 1a shows a front view of the steering wheel cover 10 of the present invention. The steering wheel cover 10 has two or more ridged sections. For convenience of illustration the steering wheel cover is divided in half by section 11 and section 12. However, it is not a necessity for there to be only two sections nor that the two or more sections are of any particular size. Sections 11 and section 12 are held together by hinge 13 which allows the two halves of the steering wheel cover 10 to be separated at the bottom making the opening between section 11 and section 12 large enough to fit over a steering wheel. Although a hinge 13 is used to provide the required flexibility of the steering wheel cover 10 any number of alternative fasteners may be substituted for the hinge 13. Draw latch 16 is used to pull the steering wheel cover 1 snuggly against the steering wheel, this too may be substituted with other fasteners. Sensors 14 monitor the position of the driver's hands on the steering wheel 10. When the hands are in an unsafe position for a pre-set time an alarm may sound, or other unpleasant, or annoying environmental changes take place, cellular devices could also be jammed as taught by Singh (U.S. Pat. No. 7,181,229) which is incorporated in its entirety by reference. Indicators 15 are used to provide visual instruction and encouragement to place the driver's hands in a safe driving position.

FIG. 1b shows the back view of the steering wheel cover 10 of the present invention. As in FIG. 1a, first section 11 and second section 12 are attached at the top by hinge 13. Sensors 14 surround the periphery of the sections and draw latch 16 joins the sections at the bottom. A compartment 17 is located in a safe and inconspicuous location. Compartment 17 contains one or more battery sockets (un-shown) to supply power to the driver safety system of the present invention that is supplemented by power from auxiliary power sources 18. Solar cells are illustrated as auxiliary power sources 18, however, electro thermal, motion and hand squeezing are among the alternatives that may be used for this purpose. A low power consumption short range transmitter receiver (un-shown) is also located in compartment 17. The five year power consumption of the system is predicted to be supplied by a button type watch battery (unshown). The short range transmitter (un-shown) receiver receives instructions from an external device to turn the power to the driver safety system of the present invention on or off depending on the speed of travel of the vehicle. No other on off switch is provided. Lack of movement of the hand position over time is considered evidence of the system being inoperable, removed or circumvented. The driver safety system can record the time, location, vehicle speed and weather conditions of any unsafe driver practice owing to the GPS connected to the external device. A signal from the one or more external devices continues to activate the bad driving habit alert for a period after hand contact has been reestablished to prevent a period of intermittent hand contact in between periods of indulging in un-safe driving habits.

FIG. 2 depicts the layers that make up the steering wheel and steering wheel cover.

The core 1 of an existing steering wheel is at the center. The next layer moving outward is the outer skin 2 of the existing steering wheel. The innermost layer 3 of the new steering wheel cover is preferably made with rubber or another highly resilient material and has raised structures to facilitate maximum grip with the steering wheel. A layer of foam rubber 4 is to give a cushion effect and to absorb minute vibrations. The spring effect that comes when the foam rubber 4 is compressed will serve as a back spring and provide pressure to hold the lock in tension. A rigid frame 5 made of fiberglass, plastic, or metal also gives strength to the steering wheel cover 10. The rigid frame 5 of the cover makes it easier to install, yet almost impossible to remove with the bear hands. The outside layer 6 is in contact with the driver's hands. This layer will is preferably made of leather, plastic, graphite, or encased gel to give the cover maximum grip, comfort, warmth and easy cleaning.

FIG. 3a shows the draw latch located in a recess 30 below the surface of section 11 and in the open position. The hook of the latch is inserted in notch 31 of section 12 followed by the latch 16 being pushed downward as shown in FIG. 3b. The installation is complete when the lock 33 of FIG. 3b engages the clasp 32 of FIG. 3a and the steering wheel cover 10 and driver safety system is secure locked in place.

I claim:

1. A steering wheel cover driver safety system, comprising:
two or more cover sections, covering a front, back and periphery of a rim of a steering wheel and for supporting the driver safety system;
two or more connecting members for immovably securing the two or more cover sections to the steering wheel;
two or more sensors configured to detect hands of a driver; and
a short range wireless transmitter for communication with one or more external devices, wherein
at least one of the two or more connecting members prevents unauthorized removal of the two or more cover sections from an outer periphery of the steering wheel; and
a signal from the one or more external devices is the only means for turning the sensors and wireless transmitter on and off.

2. The system of claim 1, wherein:
at least one of the two or more connecting members includes one or more or combinations from the list of a hinge; a draw latch; a resilient element; and a lock and key.

3. The system of claim 1, wherein:
the two or more sensors detect the positions of the hands of the driver for determining whether the hands are in a safe or unsafe position for driving.

4. The system of claim 3, wherein:
the two or more sensors detect occasional movement of the hands for determining if sensing of the true position of the hands is being circumvented.

5. The system of 1, further comprising:
a battery mount for powering at least a portion of the safety system.

6. The system of claim 5, wherein:
the battery mount accommodates a watch battery or coin cell.

7. The system of claim 1,
the signal from the one or more external devices continues to activate a bad driving habit alert for a period after hand contact has been reestablished to prevent a period of intermittent hand contact in between periods of indulging in un-safe driving habits.

8. The system of claim 1, wherein:
the short range wireless transmitter draws no power during electrically quiescent periods of the driver safety system.

9. The system of claim 1, wherein:
at least one of the two or more cover sections comprises two or more layers.

10. The system of claim 9, wherein:
at least one of the two or more layers comprise at least one from the list of: i. a ridged layer for preventing unauthorized removal of the steering wheel cover by distortion of the two or more cover sections; ii. one or more strong tensile layers with low creep coefficients for pulling the two or more cover sections into intimate contact with the steering wheel; iii. one or more compressible layers for gripping and conforming with a size variation or a shape variation of the steering wheel; iv. a flexible circuit board for electrically connecting an electrical driver safety system elements; v. an easy to clean layer; vi. a low thermal mass or low thermal conductivity layer for comfort under high temperature conditions; vii. a compressible or conformable layer for hand comfort during long trip driving; and viii. manufactured from sustainable materials or using sustainable power.

11. The system of claim 1, further comprising:
an auxiliary electrical power source taken from the list of: i. solar; ii. electro-thermal; iii. driver hand motion or pressure; iv. steering wheel turning motion; v. electrical cell between two sensors bridged by the drivers hands; and vi. non-contact connection to an external power source.

12. The system of claim 1, wherein:
the outer surface of one or more of the two or more cover sections wraps around the rim of the steering wheel by more than 180 degrees for hand comfort.

13. The system of claim 1, wherein:
sensor operation requires driver to wear electrically conductive gloves.

* * * * *